(12) United States Patent
Ogasawara

(10) Patent No.: US 9,247,863 B2
(45) Date of Patent: Feb. 2, 2016

(54) ENDOSCOPE APPARATUS WHICH CONTROLS CLAMPING OF OPTICAL BLACK INCLUDED IN AN IMAGE PICKUP SIGNAL

(71) Applicant: OLYMPUS CORPORATION, Shibuya-ku, Tokyo (JP)

(72) Inventor: Masamitsu Ogasawara, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 368 days.

(21) Appl. No.: 13/872,890

(22) Filed: Apr. 29, 2013

(65) Prior Publication Data

US 2014/0307073 A1    Oct. 16, 2014

(30) Foreign Application Priority Data

Apr. 12, 2013  (JP) ................................. 2013-084307

(51) Int. Cl.
| | |
|---|---|
| A61B 1/045 | (2006.01) |
| H04N 5/18 | (2006.01) |
| A61B 1/00 | (2006.01) |
| H04N 7/18 | (2006.01) |
| H04N 5/232 | (2006.01) |
| H04N 5/225 | (2006.01) |

(52) U.S. Cl.
CPC ......... *A61B 1/00105* (2013.01); *A61B 1/00009* (2013.01); *A61B 1/00059* (2013.01); *A61B 1/045* (2013.01); *H04N 5/185* (2013.01); *H04N 5/23203* (2013.01); *H04N 7/18* (2013.01); *H04N 7/183* (2013.01); *H04N 2005/2255* (2013.01)

(58) Field of Classification Search
CPC ........... A61B 1/00009; A61B 1/00002; A61B 1/00059; A61B 1/045; H04N 5/185; H04N 5/18
See application file for complete search history.

(56) References Cited

U.S. PATENT DOCUMENTS

| | | | | |
|---|---|---|---|---|
| 4,742,392 A | * | 5/1988 | Hashimoto | .................. 348/695 |
| 4,845,555 A | * | 7/1989 | Yabe et al. | ...................... 348/72 |
| 4,860,095 A | * | 8/1989 | Kimura et al. | .................. 348/65 |
| 5,343,245 A | * | 8/1994 | Kim | ............................. 348/257 |
| 5,434,615 A | * | 7/1995 | Matumoto | ...................... 348/72 |
| 5,585,840 A | * | 12/1996 | Watanabe et al. | ............... 348/65 |
| 5,717,457 A | * | 2/1998 | Morimoto | ..................... 348/241 |
| 5,883,987 A | * | 3/1999 | Ogoshi et al. | ................. 382/312 |
| 6,597,395 B1 | * | 7/2003 | Kim et al. | ................... 348/222.1 |
| 8,786,688 B2 | * | 7/2014 | Saito | ............................... 348/65 |
| 2007/0211839 A1 | * | 9/2007 | Suda | ............................. 375/354 |
| 2010/0271514 A1 | * | 10/2010 | Horikawa et al. | ............. 348/243 |
| 2013/0083213 A1 | * | 4/2013 | Kawada et al. | ............. 348/222.1 |

FOREIGN PATENT DOCUMENTS

JP    2001-224555 A    8/2001

* cited by examiner

*Primary Examiner* — John P Leubecker
(74) *Attorney, Agent, or Firm* — Holtz, Holtz & Volek PC

(57) ABSTRACT

An endoscope apparatus has a clamp circuit that clamps an image pickup signal that is obtained by picking up of an image with a CCD at timing that is specified with an optical black pulse, an image processing section that applies various kinds of signal processing to the image pickup signal that is outputted from the clamp circuit to convert the image pickup signal into a video signal, and a timing generator and a control section that change a phase of the optical black pulse in response to a kind of an endoscope or a length of an insertion portion.

4 Claims, 5 Drawing Sheets

FIG.3

| SCOPE ID | DELAY TIME |
|---|---|
| KIND A OF ENDOSCOPE | $\Delta t1$ |
| KIND B OF ENDOSCOPE | $\Delta t2$ |
| LENGTH C OF INSERTION PORTION | $\Delta t3$ |
| LENGTH D OF INSERTION PORTION | $\Delta t4$ |
| ⋮ | ⋮ |

32a

ENDOSCOPE APPARATUS WHICH CONTROLS CLAMPING OF OPTICAL BLACK INCLUDED IN AN IMAGE PICKUP SIGNAL

CROSS REFERENCE TO RELATED APPLICATION

This application claims the benefit of Japanese Application No. 2013-084307 filed in Japan on Apr. 12, 2013, the contents of which are incorporated herein by this reference.

BACKGROUND OF THE INVENTION

1. Field of the Invention

The present invention relates to an endoscope apparatus.

2. Description of the Related Art

Conventionally, in a medical field, endoscopes have been widely used, which are capable of observing organs inside body cavities and the like by elongated insertion portions being inserted into the body cavities, and performing various therapeutic treatments with use of treatment instruments that are inserted through insides of treatment instrument channels in accordance with necessity. Further, in an industrial field, endoscopes for industrial use are also widely used in observation and inspection of flaws, corrosion and the like in insides of boilers, turbines, engines, chemical plants and the like.

For the endoscopes for industrial use as above, endoscope apparatuses exist that are configured so that endoscopes having elongated insertion portions are attachable and detachable thereto and therefrom, and allow users to replace the endoscopes in response to inspection targets, as disclosed in Japanese Patent Application Laid-Open Publication No. 2001-224555.

In the endoscope apparatuses for industrial use as above, endoscopes having insertion portions of various lengths adapted to various inspection targets are lined up. The lengths of the insertion portions of the endoscopes correspond to a wide variety of lengths of 1 m to 30 m, and the main body sides have to be designed so that signal processing can be performed without a problem even if the endoscopes are attached thereto and detached therefrom.

Signal transmission includes transmission from the main body side to the distal end of the insertion portion, and transmission from the distal end of the insertion portion to the main body side, and therefore, a signal delay corresponding to the length which is twice as long as the insertion portion occurs. Namely since a normal electrical signal has a delay of approximately 5 nsec/m, the endoscope having the insertion portion of 1 m has a delay of 5 nsec×2=10 nsec, and the endoscope having the insertion portion of 30 m has a delay of 5 nsec×60=300 nsec.

SUMMARY OF THE INVENTION

An endoscope apparatus of one aspect of the present invention is an endoscope apparatus in which an endoscope having an insertion portion including an image pickup device at a distal end is connected to a processor apparatus, and has a clamp circuit that clamps an image pickup signal that is obtained by picking up of an image with the image pickup device at timing that is specified with an optical black pulse, an image processing section that applies various kinds of signal processing to the image pickup signal that is outputted from the clamp circuit to convert the image pickup signal into a video signal, and a phase changing section that changes a phase of the optical black pulse, in response to a kind of the endoscope or a length of the insertion portion.

BRIEF DESCRIPTION OF THE DRAWINGS

FIG. 3 is a diagram for explaining an example of a stored table of an EEPROM 32;

DETAILED DESCRIPTION OF THE PREFERRED EMBODIMENT

Hereinafter, an embodiment of the present invention will be described with use of the drawings.

Figure 1:
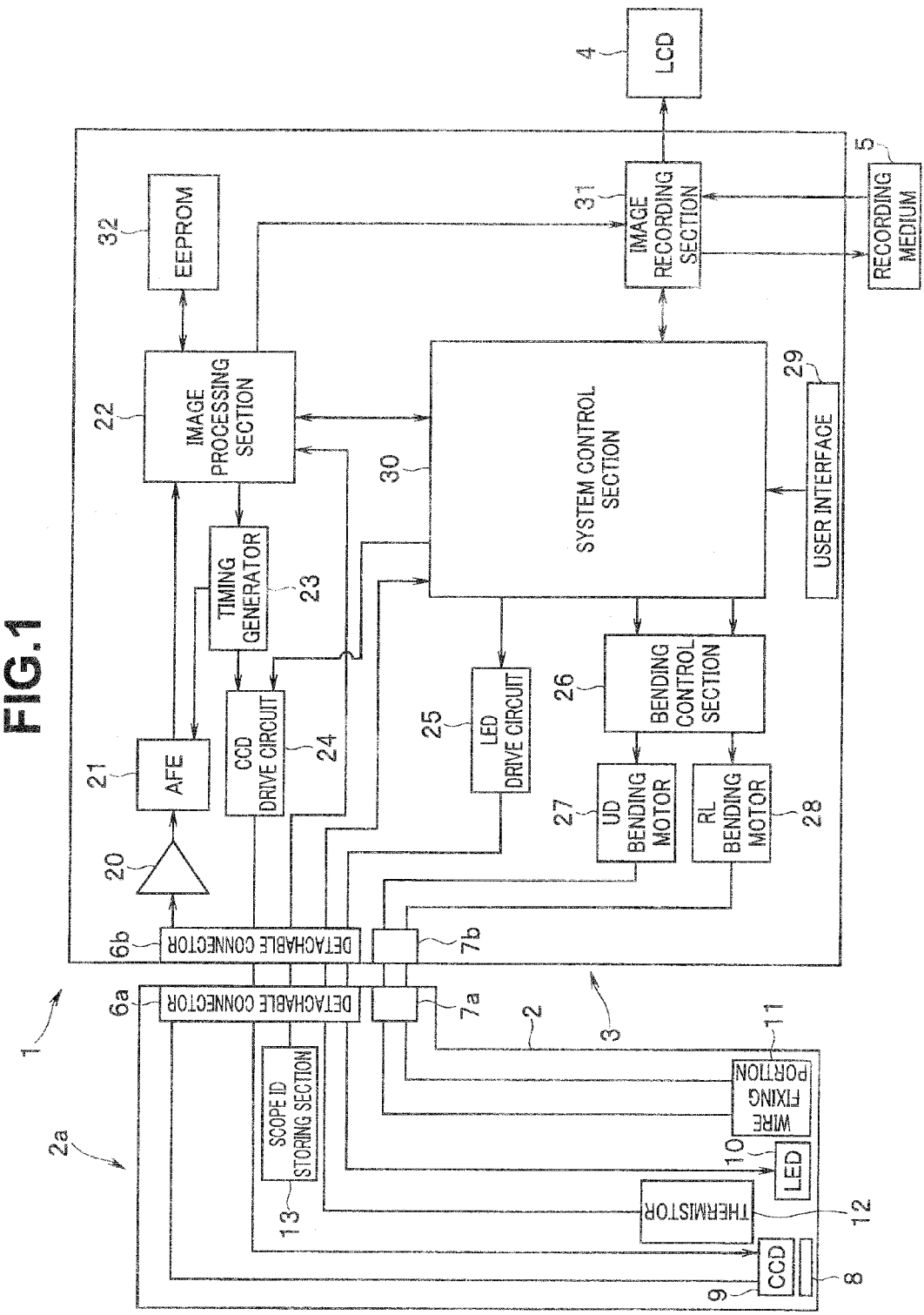
FIG. 1 is a diagram showing a configuration of an endoscope apparatus according to one embodiment of the present invention.

FIG. 1 is a diagram showing a configuration of an endoscope apparatus according to one embodiment of the present invention.

(General Configuration)

As shown in FIG. 1, an endoscope apparatus 1 is configured by having an endoscope 2a including an insertion portion 2 that is elongated and has flexibility, and a main body portion 3 as a processor apparatus to which the endoscope 2a is detachably connected, and which performs signal processing for an image pickup device loaded on the insertion portion 2 of the endoscope 2a, and an LCD 4 as a display section that displays an image picked up by the image pickup device as an endoscopic image by an image signal outputted from the main body portion 3 being inputted therein.

A recording medium 5 is made attachable to the main body portion 3, and a still image and a moving image can be recorded in the recording medium 5. Further, in an attaching and detaching portion of the endoscope 2a and the main body portion 3, detachable connectors 6a and 6b for performing electrical connection, and bending wire connection mechanisms 7a and 7b that connect bending wires are disposed.

An objective lens 8 is attached to a distal end portion of the insertion portion 2, and at an image forming position, for example, a charge coupling device (hereinafter, abbreviated as CCD) 9 is disposed as the image pickup device. Further, at a distal end portion of the insertion portion an LED 10 for illumination with which an object is illuminated, a wire fixing portion 11 that fixes a wire for bending, and a thermistor 12 that measures a temperature of the distal end portion are disposed.

Further, at a proximal end side of the insertion portion 2, a scope ID storing section 13 in which a scope ID is stored is provided. In the scope ID storing section 13 as an endoscope classification data retaining section, at least information of a kind of the endoscope 2a, or information of a length of the insertion portion 2 is retained as a scope ID. When the endoscope 2a is connected to the main body portion 3, the scope ID is read from the scope ID storing section 13, and is inputted in an image processing section 22 that will be described later.

Further, the main body portion 3 is configured by having a preamplifier 20, an analog front end (hereinafter, abbreviated as AFE) 21, the image processing section 22, a timing generator 23, a CCD drive circuit 24, an LED drive circuit 25, a bending control section 26, an UD bending motor 27, an RL bending motor 28, a user interface 29, a system control section 30, an image recording section 31, and an EEPROM 32.
(LED Control)

The LED 10 for illumination which is disposed at the distal end portion of the insertion portion 2 is connected to the LED drive circuit 25 via a cable that is inserted through an inside of the insertion portion 2. The LED drive circuit 25 is connected to the system control section 30. The LED drive circuit 25 controls lighting/extinguishing of the LED 12 by an LED lighting signal of the system control section 30. The system control section 30 receives input (ON/OFF signal of the LED 12) from the user interface 29, and controls the LED drive circuit 25.

(Bending Control)

At the distal end portion of the insertion portion 2, the wire fixing portion 11 is disposed, and four wires are connected to the wire fixing portion 11. The four wires bend the distal end portion in an upward, a downward, a leftward and a rightward directions, and two wires that control the upward and the downward directions are connected to the UD bending motor 27, and two wires that control the leftward and the rightward directions are connected to the RL bending motor 28. Note that in FIG. 1, only each wire connected to the UD bending motor 27 and the RL bending motor 28 is illustrated.

The UD bending motor 27 and the RL bending motor 28 are respectively connected to the bending control section 26. The bending control section 26 is connected to the system control section 30.

The user interface 29 is loaded with a joystick for bending that bends the distal end portion of the insertion portion 2, and when the joystick for bending is tilted in the upward and the downward directions. the system control section 30 transmits an upward and downward directions bending instruction signal to the bending control section 26. The bending control section 26 performs drive control of the UD bending motor 27 to pull the wires connected to the UD bending motor 27 based on the upward and downward directions bending instruction signal that is received. Thereby, the distal end portion of the insertion portion 2 can be bent in the upward and the downward directions.

In the same manner for bending in the leftward and the rightward directions, the system control section 30 transmits a leftward and rightward directions bending instruction signal to the bending control section 26, when the joystick for bending which bends the distal end portion of the insertion portion 2 is tilted in the leftward and the rightward directions. The bending control section 26 performs drive control of the RL bending motor 28 based on the leftward and rightward directions bending instruction signal that is received to pull the wires connected to the RL bending motor 28. Thereby, the distal end portion of the insertion portion 2 can be bent in the leftward and the rightward directions.

(Image Processing)

An image of an object illuminated with the LED 12 is formed on the CCD 9, as the image pickup section, disposed in an image forming position by the objective lens 8 disposed at the distal end portion of the insertion portion 2, and is subjected to photoelectric conversion. A composite coaxial cable that is connected to the CCD 9 is connected to the CCD drive circuit 24 and the preamplifier 20.

The CCD drive circuit 24 receives a timing signal for driving the CCD 9 from the timing generator 23. Subsequently, the CCD drive circuit 24 applies drive processing corresponding to a transmission line length (length of the composite coaxial cable) up to the CCD 9 to the timing signal which is received, and transmits the timing signal to the CCD 9 as a CCD drive signal.

The CCD 9 performs photoelectric conversion based on timing the CCD drive signal from the CCD drive circuit 24, and outputs a CCD output signal. The CCD output signal is subjected to current amplification, and thereafter, is inputted into the preamplifier 20 via the composite coaxial cable. The preamplifier 20 amplifies the CCD output signal to make up for a signal level that is attenuated by transmission by the composite coaxial cable.

The CCD output signal which is amplified by the preamplifier 20 is inputted in the AFE 21. The AFE 21 applies CDS processing (correlated double sampling processing), AGC processing (auto gain control processing), clamp processing and AD conversion processing to the CCD output signal which is amplified by the preamplifier 20, and outputs the CCD output signal to the image processing section 22. An OB pulse for clamping OB from the timing generator 23 is inputted in the AFE 21. The AFE 21 clamps OB based on the OB pulse. Note that a detailed configuration of the AFE 21 will be described with use of FIG. 2 that will be described later.

The image processing section 22 performs various kinds of image processing such as gamma correction, contour correction, white balance, electronic ZOOM, color correction, contrast correction, AE control, and freeze, and converts the CCD output signal into a video signal. The image processing section 22 performs communication with the system control section 30, the system control section 30 receives input (ZOOM signal, a Brightness signal and the like) from the user interface 29, and outputs instructions corresponding to the respective signals to the image processing section 22, and the image processing section 22 performs respective kinds of processing in accordance with the instructions. Note that a detailed configuration of the image processing section 22 will be described with use of FIG. 2 that will be described later.

(Image Recording)

The video signal outputted from the image processing section 22 is inputted in the image recording section 31. The image recording section 31 performs control of still image recording and moving image recording. The video signal which is inputted in the image recording section 31 is compressed by an encoder not illustrated in the image recording section 31, and is recorded in the recording medium 5 as a still image or a moving image. The image recording operation is performed when the system control section 30 transmits a recording signal based on the input from the user interface 29, and the image recording section 31 receives the recording signal. Note that the image recording section 31 performs still image photographing (still image recording) when the image recording section 31 performs recording after freeze of a screen is temporarily carried out, and performs moving image photographing (moving image recording) when the image recording section 31 performs recording without freeze being carried out.

Further, the still image or the moving image recorded in the recording medium 5 is expanded by a decoder not illustrated in the image recording section 31, and is outputted to the LCD 4. The image reproducing, operation is performed when the system control section 30 transmits a reproduction signal based on the input from the user interface 29, and the image recording section 31 receives the reproduction signal.

(LCD Display)

In the image recording section 31, optimal image processing that is optimal for the connected LCD 4, for example, ROB conversion processing, frame rate conversion processing and the like, is applied to the video signal inputted from the image processing section 22, and the video signal is outputted to the LCD 4. The LCD 4 displays the video signal as a display image based on the inputted video signal.

(Temperature Control)

The thermistor 12 disposed at the distal end portion of the insertion portion 2 is connected to the system control section 30 via the cable. The system control section 30 displays temperature information of the distal end of the insertion portion 2 on the LCD 4 based on information from the thermistor 12. Further, when the temperature of the distal end portion of the insertion portion 2 becomes a predetermined temperature or more, the system control section 30 displays an alarm about the temperature rise on the LCD 4.

Figure 2:
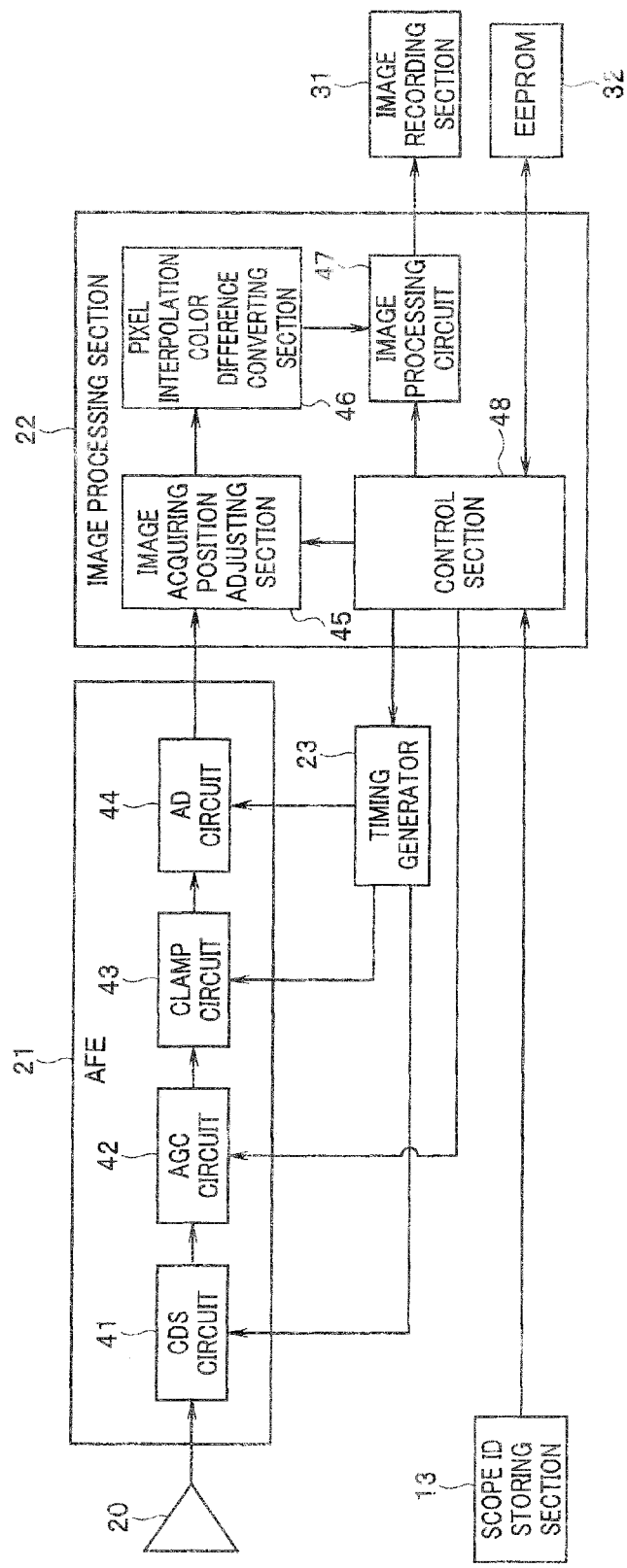
FIG. 2 is a diagram for explaining detailed configurations of an AFE 21 and an image processing section 22.

Next, the detailed configurations of the AFE 21 and the image processing section 22 will be described. FIG. 2 is a diagram for explaining the detailed configurations of the AFE 21 and the image processing section 22.

As shown in FIG. 2, the AFE 21 is configured by having a CDS circuit 41, an AGC circuit 42, a clamp circuit 43, and an AD circuit 44. Further, the image processing section 22 is configured by having an image acquiring position adjusting section 45, a pixel interpolation color difference converting section 46, an image processing circuit 47 and a control section 48.

Sampling pulses SHP and SHD are inputted in the CDS circuit 41 from the timing generator 23. The CDS circuit 41 performs correlated double sampling processing that samples a feedthrough portion and a data portion from a CCD output signal and outputs a difference of the feedthrough portion and the data portion, based on the sampling pulses SHP and SHD, and outputs a signal to the AGC circuit 42.

The AGC circuit 42 adjusts a gain of the image signal outputted from the CDS circuit 41, and outputs the signal to the clamp circuit 43, based on control from the control section 48.

An OB pulse for clamping OB from the timing generator 23 is inputted in the clamp circuit 43. The OB pulse, which will be described later, is an OB pulse which is delayed by a predetermined time in response to the kind of the endoscope 2a and the length of the insertion portion 2. The clamp circuit 43 clamps OB with the OB pulse delayed by the predetermined time. The clamp circuit 43 averages pixels of the OB which is clamped with the OB pulse to determine a black level, and outputs an image signal corresponding to the determined black level to the AD circuit 44.

The AD circuit 44 converts the image signal from the clamp circuit 43 into a digital signal, and outputs the digital signal to the image acquiring position adjusting section 45 of the image processing section 22.

The control section 48 reads a scope ID from the scope ID storing section 13, refers to a table 32a that will be described later and is stored in the EEPROM 32, and reads a delay time Δt corresponding to the scope ID. The control section 48 outputs the read delay time Δt to the timing generator 23 and the image acquiring position adjusting section 45.

The timing generator 23 generates an OB pulse with a phase (timing) of the OB pulse being changed based on the delay time Δt from the control section 48, and outputs the OB pulse to the clamp circuit 43. By the OB pulse with the phase changed in this manner, the clamp processing described above is performed by the clamp circuit 43. Note that the signal which is outputted from the timing generator 23 is not limited to the OB pulse with the phase changed, and may be a control signal for performing clamp of OB with the phase changed in response to the scope ID, for example. As above, the control section 48 and the timing generator 23 configure a phase changing section that changes the phase of an OB pulse in response to the kind of the endoscope or the length of the insertion portion.

Further, the image acquiring position adjusting section 45 adjusts a position where an effective pixel of the image pickup signal outputted from the AD circuit 44 is acquired based on the delay time Δt from the control section 48, and acquires the effective pixel. An image pickup signal of the effective pixel acquired by the image acquiring position adjusting section 45 is outputted to the pixel interpolation color difference converting section 46. As above, the control section 48 and the image acquiring position adjusting section 45 configure a position adjusting section that adjusts a position where an effective pixel of an image pickup signal is acquired, in response to the kind of the endoscope or the length of the insertion portion.

The pixel interpolation color difference converting section 46 applies pixel interpolation, and color difference converting processing to the image pickup signal from the image acquiring position adjusting section 45, and outputs the image pickup signal to the image processing circuit 47.

The image processing circuit 47 applies various kinds of image processing, for example, the gamma correction, the contour correction and the like described above to the image pickup signal from the pixel interpolation color difference converting section 46, converts the image pickup signal into the video signal and outputs the video signal to the image recording section 31.

Here, the table stored in the EEPROM 32 will be described. FIG. 3 is a diagram for explaining an example of the table stored in the EEPROM 32.

As shown in FIG. 3, in the table 32a stored in the EEPROM 32, the scope ID, and the delay time of the OB pulse corresponding to the scope ID are stored. As described above, the scope ID is, for example, information of the kind of the endoscope, or the information of the length of the insertion portion. For example, when the scope ID is a kind A of the endoscope, Δt1 is assigned as the delay time, and when the scope ID is a kind B of the endoscope, Δt2 is assigned as the delay time. Likewise, when the scope ID is a length C of the insertion portion, Δt3 is assigned as the delay time, and when the scope ID is a length D of the insertion portion, Δt4 is assigned as the delay time.

When the control section 48 reads the scope ID from the scope ID storing section 13, the control section 48 refers to the table 32a, and reads the delay time Δt corresponding to the scope ID. For example, when the scope ID is the length C of the insertion portion 2, the control section 48 reads the delay time Δt3, and outputs the read delay time Δt3 to the timing generator 23 and the image acquiring position adjusting section 45. Thereby, the clamp processing by the OB pulse corresponding to the scope ID described above, and adjustment of the position where the effective pixel is acquired are performed.

Next, an operation of the endoscope apparatus 1 configured as above will be described.

Figure 4:
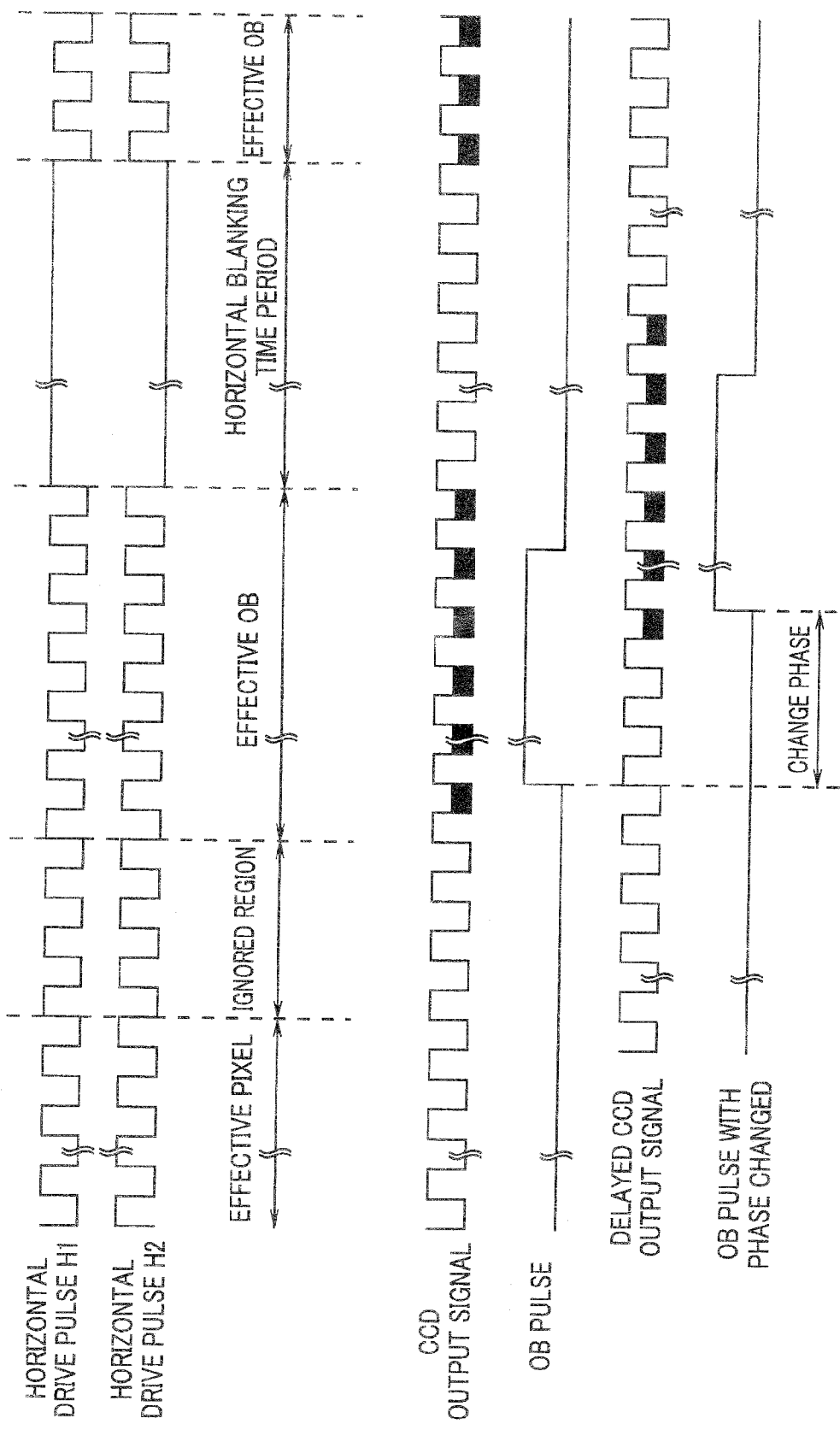
FIG. 4 is a timing chart for explaining an operation of an endoscope apparatus 1.

FIG. 4 is a timing chart tor explaining the operation of the endoscope apparatus 1.

Horizontal drive pulses H1 and H2 with outputs thereof being reversed from each other arc outputted from the CCD drive circuit 24 to the CCD 9, whereby a CCD output signal is outputted to the main body portion 3. In the CCD output signal, an effective pixel, an ignored region and a pixel of effective OB are present The effective OB is clamped with an OB pulse, whereby a black level is obtained.

However, when the insertion portion 2 is long, a delay occurs to the CCD output signal. If the delayed CCD output signal is clamped with the aforementioned OB pulse, the pixels which are not of the effective OB are also clamped, and an accurate black level cannot be obtained.

Thus, the control section 48 reads the delay time Δt corresponding to the scope ID from the table 32a, and outputs the delay time Δt to the timing generator 23. Subsequently, the timing generator 23 generates the OB pulse with a phase thereof changed based on the delay time Δt read by the control section 48 and outputs the OB pulse to the clamp circuit 43. Thereby, the effective OB of the delayed CCD output signal can be accurately clamped, and therefore, an accurate black level can be obtained.

Figure 5:
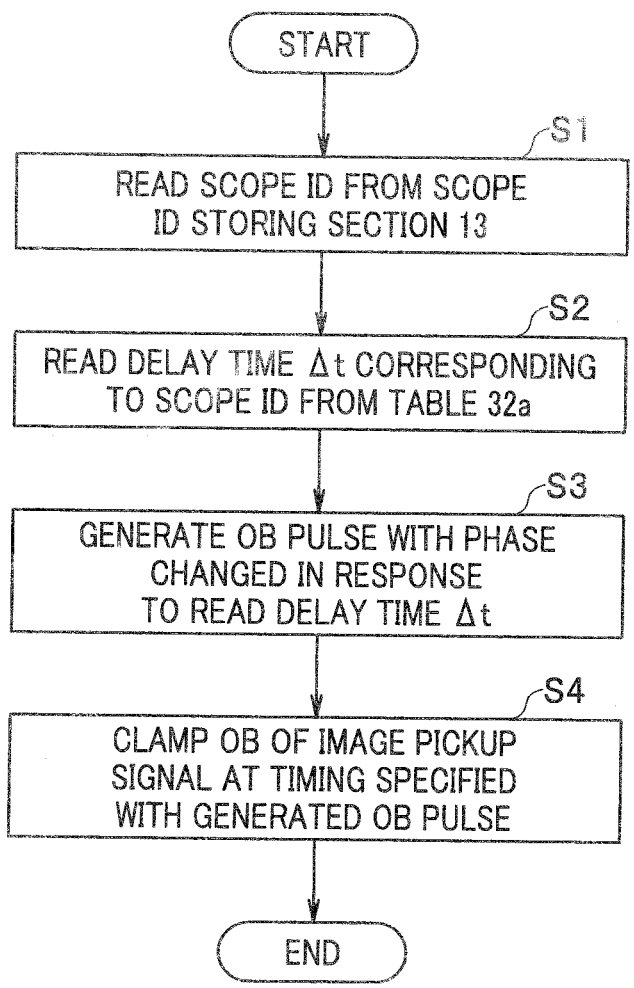
FIG. 5 is a flowchart showing a flow of clamp processing of the endoscope apparatus 1 according to the embodiment of the present invention.

FIG. 5 is a flowchart showing an example of a flow of the clamp processing of the endoscope apparatus 1 according to the embodiment of the present invention.

First, when the endoscope 2a is connected to the main body portion 3, the scope ID of the scope ID storing section 13 is read (step S1). Next, the delay time Δt corresponding to the read scope ID is read from the table 32a (step s2). Next, the OB pulse with the phase changed in response to the read delay time Δt is generated (step S3). Finally, the OB of the image pickup signal is clamped at timing specified with the generated OR pulse (step S4), and the processing is finished.

As above, the endoscope apparatus 1 reads the scope ID of the endoscope 2a which is connected to the main body portion) from the scope ID storing section 13, and reads the delay time corresponding to the scope ID from the table 32a of the EEPROM 32. Subsequently, the endoscope apparatus 1 changes the phase of the OB pulse with which the effective OB is clamped based on the read delay time, and clamps OB with the OB pulse with the phase being changed. As a result, the endoscope apparatus 1 can accurately clamp the effective OB of the CCD output signal which is delayed in response to the length of the insertion portion 2 or the like.

Therefore, according to the endoscope apparatus of the present embodiment, OB can be accurately clamped irrespective of the kind of the endoscope and the length of the insertion portion.

Note that, as for the respective steps in the flowchart in the present description, the execution sequence may be changed, a plurality of the steps may be simultaneously executed, or the respective steps may be executed in a different sequence at each execution, unless it runs counter to the nature thereof.

The present invention is not limited to the embodiment described above, and various modifications, alterations and the like can be made within the range without departing from the gist of the present invention.

What is claimed is:

1. An endoscope apparatus in which an endoscope having an insertion portion including an image pickup device at a distal end is connected to a processor apparatus, the endoscope apparatus comprising:
    a clamp circuit that clamps optical black included in an image pickup signal that is obtained by picking up of an image with the image pickup device at timing that is specified with an optical black pulse;
    an image processing section that applies various kinds of signal processing to the image pickup signal that is outputted from the clamp circuit to convert the image pickup signal into a video signal;
    a phase changing section that changes a phase of the optical black pulse, in response to a kind of the endoscope or a length of the insertion portion; and
    a position adjusting section that adjusts a position where an effective pixel of the image pickup signal is acquired, in response to the kind of the endoscope or the length of the insertion portion.

2. The endoscope apparatus according to claim 1, further comprising:
    an endoscope classification data retaining section that stores information of the kind of the endoscope or the length of the insertion portion.

3. The endoscope apparatus according to claim 1, wherein the endoscope is detachably connected to the processor apparatus.

4. The endoscope apparatus according to claim 1, wherein the clamp circuit determines a black level from optical black clamped by an optical black pulse subjected to phase-change, and outputs an image pickup signal corresponding to the determined black level.

* * * * *